United States Patent [19]

Süess et al.

[11] Patent Number: 6,024,968
[45] Date of Patent: Feb. 15, 2000

[54] INTERSORPTION COMPOSITION AND METHOD

[75] Inventors: Hans R. Süess, Dulliken, Switzerland; Howard L. Lene, Vaduz, Liechtenstein

[73] Assignee: Lincoln Technologies Inc., Westport, Conn.

[21] Appl. No.: 08/420,975

[22] Filed: Apr. 10, 1995

Related U.S. Application Data

[63] Continuation-in-part of application No. 07/983,480, Dec. 3, 1992, abandoned, which is a continuation-in-part of application No. 07/746,392, Aug. 16, 1991, abandoned.

[51] Int. Cl.⁷ .............................. A61K 7/021; A61K 9/14
[52] U.S. Cl. ........................... 424/401; 424/63; 424/484; 424/486
[58] Field of Search ...................... 424/484, 486, 424/70.12, 70.31, 401, 63

[56] References Cited

U.S. PATENT DOCUMENTS

| | | | |
|---|---|---|---|
| 4,364,837 | 12/1982 | Pader | 252/173 |
| 4,906,459 | 3/1990 | Cobb | 424/70 |
| 5,085,854 | 2/1992 | Fukuda et al. | 424/63 |
| 5,338,536 | 8/1994 | Thimineur | 424/70.12 |

FOREIGN PATENT DOCUMENTS

| | | |
|---|---|---|
| 0 197 485 | 10/1986 | European Pat. Off. . |
| 0 359 488 | 3/1990 | European Pat. Off. . |
| 0 388 582 | 9/1990 | European Pat. Off. . |
| WO 92/00077 | 1/1992 | WIPO . |

*Primary Examiner*—Thurman K. Page
*Assistant Examiner*—Sharon Howard
*Attorney, Agent, or Firm*—Christensen O'Connor Johnson & Kindness PLLC

[57] ABSTRACT

Active ingredients are solubilized or dispersed in a matrix which also contains dispersants. When this composition is applied to a permeable substrate, the matrix and dispersants associate with the substrate and bring the active ingredient into contact with the substrate while substantially preventing penetration of the active ingredient into the permeable substrate. The consistent and continuous contact of the active ingredient with the permeable substrate, needed to achieve optimal and reliable effectiveness of the active ingredient, is enhanced by the low water solubility of the composition and by its resistance to removal by rubbing. The composition is, however, easily removable by surface active agents, such as soaps and detergents.

51 Claims, No Drawings

INTERSORPTION COMPOSITION AND METHOD

CROSS REFERENCE TO RELATED APPLICATIONS

This is a continuation-in-part of U.S. patent application Ser. No. 07/983,480, filed on Dec. 3, 1992 now abandoned, which is a continuation-in-part of U.S. patent application Ser. No. 07/746,392, filed on Aug. 16, 1991 and now abandoned.

TECHNICAL FIELD

The present invention comprises a composition and method for delivering an active ingredient to the surface of a permeable substrate wherein the composition substantially prevents penetration of the active ingredient into the permeable substrate.

BACKGROUND OF THE INVENTION

The term "intersorption" composition as used herein means a matrix, a dispersant and an active ingredient, such that the matrix and the dispersant substantially prevent penetration of the active ingredient into a substrate while maintaining the active ingredient in intimate contact with the surface of the permeable substrate.

The term "permeable substrate" as used herein means a surface including, but not limited to, human skin, animal skin, human hair, animal hair, nails, leather, plants, wood, ceramic, metal, plastic, and synthetic materials.

The term "active ingredient" as used herein means a substance used to create a beautifying, cleansing, protecting or medicating effect.

The term "hydrophilic-lipophilic balance (HLB)" as used herein denotes the relative balance of hydrophilic (water loving) and lipophilic (oil-loving) characteristics of a component. HLB values run from approximately 1 to 50. Low HLB indicates a component has poor water dispersibility/solubility and good oil dispersibility/solubility. High HLB indicates a component has good water dispersibility/solubility and poor oil dispersibility/solubility. HLB increases as the water dispersibiity/solubility of the component increases and the oil dispersibility/solubility of the component decreases (Remington's Pharmaceutical Sciences, 16th Edition, Mack Publishing Co., Philadelphia, Pa., pgs. 263–265 & 316–319).

Permeable substrates are subject to a variety of external insults which result in drying, cracking, dulling, peeling, swelling, splitting, corrosion, erosion, and a variety of other problems. Human skin is especially vulnerable to environmental agents which cause irritation, erosion, maceration, burning, drying, cracking and peeling.

Absorption of an active ingredient into a permeable substrate also can create problems. Application of cosmetic and medicinal preparations to the surface of human skin or to the surface of animal skin can result in absorption of the active ingredient into the epidermal layer. Epidermal absorption of a colored active ingredient can result in temporary or permanent discoloration of the skin. Epidermal absorption of an odoriferous active ingredient can result in sustained malodors from the skin. Further, epidermal absorption of active ingredients can result in, among other things, irritation, itching, burning and allergic reactions and in mutagenic, teratogenic and carcinogenic manifestations.

Application of an active ingredient to a permeable substrate other than skin including, but not limited to, human hair, animal hair, nails, leather, plants, wood, plastic, ceramic, metal and synthetic materials can result in absorption of the active ingredient into its respective permeable substrate. Again, absorption of a colored active ingredient can result in temporary or permanent discoloration. Further, absorption of an active ingredient can result in, among other things, swelling, cracking, peeling, splitting, dulling, and crazing.

An active ingredient most often is applied to a permeable substrate after being dissolved or dispersed in a carrier. Most carriers are either hydrophilic or hydrophobic. Hydrophilic carriers are readily soluble in water and are readily removed by water. Hydrophobic carriers are not readily soluble in water and are not readily removed by water. Moreover, neither hydrophilic nor hydrophobic carriers prevent the active ingredient they are carrying from being absorbed into the permeable substrate to which they are applied.

An active ingredient dissolved or dispersed in a hydrophilic carrier can be applied to a permeable substrate easily, but has the disadvantage of being removed from the permeable substrate easily by the slightest contact with water such as by washing, by perspiring or by swimming. Further, an active ingredient dissolved or dispersed in a hydrophilic carrier, which includes most cosmetic preparations, must be maintained and reapplied on a continuing basis. An active ingredient dissolved or dispersed in a hydrophobic carrier also can be applied to a permeable substrate easily, but has the disadvantage of being difficult to remove from the permeable substrate. Further, an active ingredient dissolved or dispersed in a hydrophobic carrier, which includes many protectants used on permeable substrates exposed to water on a continuous or intermittent basis, is greasy, tacky and cosmetically unsatisfactory.

What is needed is a composition and method wherein a carrier brings an effective amount of an active ingredient into intimate association with a permeable substrate such that the active ingredient is fixed within the carrier and such that the carrier substantially prevents penetration of the active ingredient into the permeable substrate. Such a composition must not be easily removable by water or by rubbing, but must be easily removable from the permeable substrate.

SUMMARY OF THE INVENTION

As will be seen, the present invention overcomes these and other problems associated with prior art methods of delivering an active ingredient to a permeable substrate. The intersorption composition and method of the present invention comprises a matrix having a viscosity between approximately 40 centipoise and approximately 20,000 centipoise, a dispersant having an average hydrophilic-lipophilic balance (HLB) between approximately 14 and 22, and an active ingredient such that, when applied to a permeable substrate, the matrix and the dispersant substantially prevent penetration of the active ingredient into the permeable substrate.

When the intersorption composition of the present invention is applied to a permeable substrate, the matrix and dispersant bind to various hydrophilic, lipophilic, proteophilic and other components of the permeable substrate while, simultaneously, the matrix and the dispersant imprison the active ingredient such that the active ingredient contacts the permeable substrate but, unexpectedly, is substantially prevented from penetrating into the permeable substrate. Thus, the active ingredient will appear as if it is part of the permeable substrate even though it is not bonded to the permeable substrate or absorbed into the permeable substrate.

In the intersorption composition and method of the present invention, the consistent and continuous contact of the active ingredient with the permeable substrate, needed to achieve optimal and reliable effectiveness of the active ingredient, is enhanced by the viscosity and the HLB of the intersorption composition of the present invention. This enables the intersorption composition to remain in contact with the permeable substrate during washing, swimming and sweating. Further, the intersorption composition is not removed easily from the permeable substrate by rubbing. However, the intersorption composition is removed easily from the permeable substrate by surface active agents such as soaps and detergents.

Further, the intersorption composition and method of the present invention, provides a composition and method for protecting a permeable substrate against environmental insult by its unique ability to contact the permeable substrate to form an essentially invisible, greaseless, tackless, colorless and odorless protective guard which retards interaction of moisture, oil, dirt, grease, irritants, pollutants, radiation and the like with the permeable substrate.

Accordingly, it is an object of the present invention to provide an intersorption composition and method that maintains an active ingredient in contact with the surface of a permeable substrate while substantially preventing penetration of the active ingredient into the permeable substrate.

It is another object of the present invention to provide an intersorption composition that protects a permeable substrate from environmental insult.

It is another object of the present invention to provide an intersorption composition that contacts a permeable substrate.

It is another object of the present invention to provide an intersorption composition that is essentially odorless, transparent and greaseless.

It is another object of the present invention to provide an intersorption composition that is not obvious to sight or touch.

It is another object of the present invention to provide an intersorption composition that does not form a visible edge.

It is another object of the present invention to provide an intersorption composition that is resistant to removal by water.

It is another object of the present invention to provide an intersorption composition that is resistant to removal by rubbing.

It is another object of the present invention to provide an intersorption composition that is easily removable with a surfactant.

It is another object of the present invention to provide an intersorption composition that is easily applicable to a permeable substrate.

It is another object of the present invention to provide an intersorption composition that is easily applicable to human skin and to animal skin.

It is another object of the present invention to provide an intersorption composition that is easily applicable to human hair and animal hair.

It is another object of the present invention to provide an intersorption composition that is easily applicable to nails.

It is another object of the present invention to provide an intersorption composition that is easily applicable to plant, wood, plastic, ceramic, metal and synthetic materials.

It is another object of the present invention to provide an intersorption composition and method to deliver an effective amount of a pharmaceutically active ingredient to a permeable substrate while substantially preventing penetration of the pharmaceutically active ingredient into the permeable substrate.

It is another object of the present invention to provide an intersorption composition and method to deliver an effective amount of a coloring ingredient to a permeable substrate while substantially preventing penetration of the coloring ingredient into the permeable substrate.

It is another object of the present invention to provide an intersorption composition and method to deliver an effective amount of a cosmetically active ingredient to a permeable substrate while substantially preventing penetration of the cosmetically active ingredient into the permeable substrate.

It is another object of the present invention to provide an intersorption composition and method to deliver an effective amount of a tanning ingredient to a permeable substrate while substantially preventing penetration of the tanning ingredient into the permeable substrate.

It is another object of the present invention to provide an intersorption composition and method to deliver an effective amount of a fragrance ingredient to a permeable substrate while substantially preventing penetration of the fragrance ingredient into the permeable substrate.

It is another object of the present invention to provide an intersorption composition and method to protect human skin and animal skin from irritating and damaging agents.

It is another object of the present invention to provide an intersorption composition and method to protect human skin and animal skin from radiation, ultraviolet light, bacteria, and parasites.

It is another object of the present invention to provide an intersorption composition and method to protect human hair and animal hair from damaging and dulling agents.

It is another object of the present invention to provide an intersorption composition and method to enhance the uniformity and brilliance of human hair and animal hair colorants.

It is another object of the present invention to provide an intersorption system that enhances the luster and surface smoothness of human hair and animal hair.

It is another object of the present invention to provide an intersorption composition and method to enhance, protect and beautify wood grain, texture, and pores.

It is another object of the present invention to provide an intersorption composition and method to enhance, protect, and beautify a plastic surface.

It is another object of the present invention to provide an intersorption composition and method to enhance, protect, and beautify a metal surface.

It is another object of the present invention to provide an intersorption composition and method to enhance, protect, and beautify a ceramic surface.

It is another object of the present invention to provide an intersorption composition and method to protect a metal surface against attack by corrosion, oxidation, and acid.

It is another object of the present invention to provide an intersorption composition and method to protect a plant, leather, wood, plastic, ceramic, metal, and synthetic material against radiation, drying, mildew, bacteria and parasites.

These and other objects, features and advantages of the present invention will become apparent after a review of the following detailed description of the disclosed embodiments and the appended claims.

DETAILED DESCRIPTION

The present invention is a composition and method for contacting an active ingredient with a permeable substrate such that the active ingredient is substantially prevented from penetrating the permeable substrate.

The intersorption composition of the present invention comprises a matrix having a viscosity between approximately 40 centipoise and approximately 20,000 centipoise, a dispersant having an average hydrophilic-lipophilic balance (HLB) between approximately 14 and approximately 22 and an active ingredient such that the matrix and the dispersant imprison the active ingredient within the composition and substantially prevent penetration of the active ingredient into a permeable substrate. When the intersorption composition is applied to a permeable substrate, the matrix and dispersant bind to the permeable substrate and enable an effective amount of the active ingredient to contact the permeable substrate while the matrix and the dispersant substantially prevent penetration of the active ingredient into the permeable substrate. Other components which alter the properties of the matrix, of the dispersant, of the active ingredient, and of their interactions can be included in the intersorption composition of the present invention.

The intersorption composition of the present invention is not easily removable from the permeable substrate by contact with water or by rubbing, but is easily removable from the permeable substrate by surface active agents such as soaps and detergents.

The matrix of the intersorption composition of the present invention comprises non-volatile and slowly volatile components. These non-volatile and slowly volatile components bind to hydrophilic, lipophilic, proteophilic and other components of a permeable substrate to hold the active ingredient in contact with the permeable substrate. Simultaneously, these non-volatile and slowly volatile components imprison the active ingredient and substantially prevent penetration of the active ingredient into the permeable substrate.

These non-volatile and slowly volatile components include, but are not limited to, lipids, waxes and semisolids and their derivatives; heavier fractions of petroleum and hydrocarbons and their derivatives; pure and modified silicone polymers; and, combinations of the above. These can be synthetically derived or naturally occurring.

Lipids, waxes and semisolids include, but are not limited to, ceramides, sphingolipids, wax and sterol esters, extracellular membrane lipids, intracellular membrane lipids, ganglionic membrane lipids, and intracellular lipids and their derivatives. Bioengineered lipids, waxes, and semisolids include, but are not limited to, those derived genetically from reproducing organisms and their derivatives and those derived synthetically from reproducing organisms and their derivatives. Synthetically derived lipids, waxes and semisolids include, but are not limited to, polyethylene waxes, squalene, jojoba oil, and hydrogenated jojoba oil.

Heavier fractions of petroleum and hydrocarbons and their derivatives include, but are not limited to, waxes, high molecular weight petroleum fractions, white and colored petrolatums and petrolatum fractions having a low white oil content.

Pure and modified silicone polymers include, but are not limited to, silicone polymers and silicone polymers modified by the addition of backbone, cross-linking and functional groupings. These include, but are not limited to, dimethyl/trimethyl/polysiloxane, dimethicone, polysiloxane polyether copolymer, and amido and other hydrophilic modified silicones.

The percentage of non-volatile and slowly volatile components of the matrix of the present invention is between approximately 0.1% and 50% with a preferred concentration range between approximately 1% and 20%. The viscosity range of individual non-volatile and slowly volatile components for use in the matrix of the present invention is between approximately 1 centapoise and approximately 20,000 centapoise with a preferred viscosity range between approximately 2 centapoise and approximately 15,000 centapoise. The viscosity of mixtures of non-volatile and slowly volatile components of the matrix for use in the present invention is between approximately 10 centapoise and approximately 13,000 centapoise with a preferred average viscosity between approximately 50 centapoise and approximately 3,000 centapoise and with a more preferred average viscosity between approximately 100 centapoise and approximately 1,000 centapoise.

Dispersants for use in the intersorption composition of the present invention enhance the imprisonment of the active ingredient within the matrix to further substantially prevent penetration of the active ingredient into the permeable substrate. Dispersants include, but are not limited to, anionic agents such as alkyl sulfonates and alkyl phosphates; non-ionic agents such as polysorbates and high ethoxylation polyoxyethylene esters and ethers; amphoteric agents such as alkyl imidazolines and acyl peptides; cationic agents such as ethoxylated alkyl dimethyl ammonium salts; sorbitan fatty acid esters; polyethylene glycol stearate and oleate esters; polyethylene glycol lauryl and cetyl ethers; polysorbate 20 and polysorbate 40; sodium lauryl sulfates; ceteareth 3 and 6; and, caprylyl and lauryl pyrrolidones.

The amount of dispersant for use in the intersorption composition of the present invention is between approximately 0.1% and 20% with a preferred amount between approximately 0.2% and 10%. The average amount of dispersants for use in the present invention is between approximately 5% and 20% with a preferred average amount between approximately 8% and 14%. The HLB of a dispersant for use in the intersorption composition of the present invention is between approximately 2 and 45 with a preferred HLB between approximately 3 and 40. The average HLB of the dispersants for use in the present invention is between approximately 10 and approximately 25 with a preferred average HLB between approximately 14 and 21.

The matrix and the dispersants contact and associate with hydrophilic, and lipophilic components of a permeable substrate. When the matrix and the dispersants are associated with the permeable substrate, they appear essentially imperceptible or they appear acceptably perceptible to the user. Quantified tests for measuring these qualities include, but not limited to, tests for visibility, tackiness, greasiness and surface distortion which are known to those skilled in the art. These tests enable determination of the visibility and acceptability of the intersorption composition of the present invention on the surface of a permeable substrate.

Active ingredients for use in the intersorption composition of the present invention are imprisoned within the matrix and dispersants. Therefore, when they contact a permeable substrate, migration of the active ingredient out of the intersorption composition is inhibited and the active ingredient does not penetrate substantially into the permeable substrate. Active ingredients for use in the intersorption composition of the present invention encompass a wide range of ingredients which benefit or enhance a permeable substrate by being brought into association with the permeable substrate while being substantially prevented from penetrating into the permeable substrate. Such active ingredients include, among others, those used to create beautifying, cosmetic, cleansing, protective, and medicinal effects.

Active ingredients for use in the intersorption composition of the present invention include, but are not limited to, ingredients which increase sheen; decrease sheen; absorb oil; absorb moisture; retard moisture loss; retard oil loss; retard loss of volatile substances; retard loss of erodible substances; repel, entrap, disperse, inhibit, destroy or dissipate water, moisture, vapor, oils, gases, microbes, insects, viruses and other like substances; certified and industrial colors, dyes, pigments, iridescent, liquid crystals, biocolors, color developing, and color enhancing systems; heat, irradiation, and other energy absorbing, protecting, dissipating and repelling materials; agents which protect against oxidation, reduction, corrosion and other exogenous or endogenous assaults; smoothing and tightening agents; fragrances and other odoriferous substances; agents which absorb, prolong and modify odoriferous and malodorous substances; cosmetic agents; conditioning agents; medicinal agents; insecticides; pediculocides; polishing, surface enhancing, surface restoring, wear reducing, and damage protecting agents; and, combinations of the above.

A fragrance is one example of an active ingredient which can be used in the intersorption composition and method of the present invention. Fragrance materials bind to protein and to lipid components of human skin and of animal skin and to protein, lipid, cellulose and other components of other permeable substrates. This binding results in loss of fragrance intensity and often to undesirable changes in fragrance character. This can occur with either a single fragrance ingredient or with mixtures of fragrance ingredients as found in most finished fragrances. This results in diminished consumer satisfaction. When fragrance materials are used as the active ingredient in the intersorption composition of the present invention, the matrix and the dispersants of the intersorption composition substantially prevent the fragrance from penetrating into the permeable substrate and, therefore, fragrance intensity and character are protected. Further, the intersorption composition of the present invention can control the rate and intensity of fragrance release. This, in turn, can increase consumer satisfaction. Single fragrances, mixtures of fragrances, deodorizing substances, and substances that entrap or incapacitate odoriferous agents all can be used as the active ingredient in the intersorption composition of the present invention.

An insect repellent is another example of an active ingredient which can be used in the intersorption composition and method of the present invention. Insect repellents often are lost from the surface of human skin and of animal skin by absorption and surface attrition. When insect repellents, such as N,N-diethyl-m-toluamide, are applied to a permeable substrate as the active ingredient within the intersorption composition of the present invention they are not lost by absorption and surface attrition.

The intersorption composition and method of the present invention also can be used to protect a permeable substrate by reducing absorption of oxidizing agents such as inorganic and organic peroxides; aldheydes such a glutaraldehyde; rubefacients such as histamine dihydrochloride; and, potentially irritating but very useful fragrance agents such as cinnamic alcohol and aldehyde, essence of sassafras, and essence of pine. Further, the intersorption composition and method of the present invention can be used to protect leather, plant, wood, plastic, ceramic, metal, and synthetic materials from erosion, corrosion, oxidation, acid attack, radiation damage, mildew, bacteria and parasites.

The concentration range of the active ingredient for use in the intersorption composition and method of the present invention is between approximately 0.001% and 25% with a preferred concentration range between approximately 0.003% and 10%.

Other agents can be included in the intersorption composition of the present invention. Such components include, but are not limited to, gelling agents such as carbomers, alginates, synthetic cellulose, acrylic gums, natural gums, and aluminum fatty acids; buffers such as acetate, citrate, alpha hydroxy acids and phosphates; humectants, emollients, and softening agents such as polypropylene glycol, glycerin, butylene glycol, ethylene glycol, sorbitol, mannitol and pentaerythritol; aromatics such as menthol, camphor, methyl salicylate, and eugenol; fragrances; spices; colorants; dyes; and pigments; preservatives such as parabens, benzoic acid, sorbic acids, aldehydes, aldehyde donors, imidazolidinyl urea, methychloro-isothizolinone, and methylisothizxolinone; and, antioxidants such as bisulfites, tocopherols, propyl gallate and thiols; and, combinations of the above.

Volatile components also can be included in the intersorption composition of the present invention to ease application of the intersorption composition to the permeable substrate, to produce a cooling effect, and to create sensate effects. Volatile components include, but are not limited to, volatile fluorocarbons; volatile halocarbons; silicones such as cyclomethicone; volatile silicone derivatives; ethers such as dibutyl ether; alcohols such as ethanol, sorbitol and isopropanol; esters such as ethyl acetate; ketones such as methyl ethyl ketone; and, combinations of the above.

The present invention is further illustrated by the following examples, which are not to be construed in any way as imposing limitations upon the scope thereof. On the contrary, it is to be clearly understood that resort may be had to various other embodiments, modifications and equivalents thereof which, after reading the description herein, may suggest themselves to those skilled in the art without departing from the spirit of the present invention and/or the scope of the appended claims.

EXAMPLE 1

Example 1 illustrates the intersorption composition and method of the present invention wherein the active ingredient is gentian violet. Gentian violet is an effective antimicrobial agent whose use on skin has been limited because its stains the skin a deep, long-lasting purple color.

The intersorption system comprises the matrix components jojoba oil and dimethicone (ultra high viscosity); the active ingredient gentian violet; solubilizers to solubilize the gentian violet; dispersants to further impede gentian violet diffusion out of the matrix; a preservative; and a volatile component.

Table 1 includes each ingredient and its amount.

TABLE 1

| Matrix | | Viscosity |
| --- | --- | --- |
| Jojoba Oil | 2.0% | 40 cps |
| Dimethicone, ultra high viscosity | 1.56% | 12500 cps |
| | | Mixture = |
| | | 150 cps |
| Dispersants | | HLB Value |
| PEG-40 stearate ester | 1.5% | 16.9 |
| PEG-25 lauryl ether | 1.5% | 16.9 |
| Polysorbate-20 | 3.0% | 16.7 |
| Polysorbate-40 | 3.0% | 15.6 |
| Ceteareth-3 | 0.4% | 6.0 |
| Ceteareth-6 | 0.2% | 9.5 |
| | Total = | Average = |
| | 9.6% | 15.8 |
| Active Ingredient | | |
| Gentian Violet | 0.5% | 0.5% |
| Solubilizers for Gentian Violet | | |
| Glycerol | 3.0% | |
| Glycereth 26 | 2.0% | |
| Water | 10.85% | |
| Preservative | | |
| Methylchloroisothiazolinone | 0.05% | |
| Volatile Component | | |
| Cyclomethicone, volatile D4 or D5 or mixture | 70.44% | |

The concentration of all components is expressed as percent by weight. The gentian violet is dissolved in solubilizers at 38–42° C. with constant stirring. When the gentian violet is dissolved, the dispersants and the preservative are added. The preparation is covered and the matrix components and the volatile component are added. Stirring is continued until the preparation is uniform and is cooled to room temperature. The formulation can be spread directly and easily on a substrate such as skin.

Human Skin Tests

Five human volunteers are used in this study. A square, four inches per side, is outlined with surgical tape on the left arm and on the right arm of each subject. A solution of gentian violet, prepared by dissolving 50 milligrams of gentian violet in 100 milliliters of 50% ethanol-50% water, is applied to the square on the left arm of each subject. The intersorption composition of Example 1 is applied to the square on the right arm of each subject. After four hours, both arms of each subject are washed with a detergent solution. The square on the left arm is colored a deep purple. The square on the right arm is colored an almost imperceptible violet.

EXAMPLE 2

Example 2 illustrates the intersorption composition and method of the present invention wherein the active ingredients are organic dye colorants.

The intersorption composition comprises the matrix components squalene and dimethicone (ultra high viscosity); the active ingredients organic dyes FD&C Red No. 33, Yellow No. 5 and Blue No. 1; solubilizers to solubilize the organic dyes; dispersants to further impede organic dye diffusion out of the matrix; a preservative; and a volatile component.

Table 2 includes each ingredient and its amount.

TABLE 2

| Matrix | | Viscosity |
| --- | --- | --- |
| Squalene | | 35 cps |
| Dimethicone, ultra high viscosity | 1.8% | 12,500 cps |
| | | Mixture = |
| | | 135 cps |
| Dispersants | | HLB Value |
| PEG-36 Oleate ester | | 16.9 |
| PEG-20 Cetyl ether | 1.4% | 15.7 |
| Polysorbate-20 | 1.6% | 16.7 |
| Sodium Lauryl Sulfate | 6.2% | 40.0 |
| Caprylyl Pyrroliodone | 1.4% | 6.0 |
| Lauryl Pyrroliodone | 0.8% | 3.0 |
| | 1.0% | Average = |
| | Total = | 17.4 |
| | 12.4% | |
| Active Ingredients | | |
| FD&C Red No. 33 | 0.033% | |
| FD&C Yellow No. 5 | 0.064% | |
| FD&C Blue No. 1 | 0.003% | |
| Organic Dye Solubilizers | | |
| Propylene Glycol | | |
| Water | 3.0% | |
| Preservative | 11.8% | |
| Imidazolidinyl Urea | | |
| Water | | |
| | 0.2% | |
| | 2.0% | |
| Volatile Component | | |
| Cyclomethicone, volatile D4 or D5 or a mixture | 67.4% | |

The concentration of all components is expressed as percent by weight. The organic dyes FD&C Red No. 33, Yellow No. 5 and Blue No. 1 are dissolved in solubilizers at 38–42° C. with constant stirring. When the organic dyes are dissolved, the dispersants and the preservative are added. Next the matrix components are added. The preparation is covered and the volatile component is added. Stirring is continued until the preparation is uniform and is cooled to room temperature. The formulation can be spread directly and easily on a permeable substrate such as skin.

Human Skin Tests

The formulation of Example 2 is applied by four volunteers to the skin on their faces. As judged by these volunteers, this intersorption composition is easy to apply, is uniform in appearance and provides exceptionally natural coloration without staining, streaking or caking. The intersorption composition retains these characteristics until it is removed by washing with soap and water eight hours after its application.

EXAMPLE 3

Example 3 illustrates the intersorption composition of the present invention wherein the active ingredients pigments, a UV dispersant, and a free radical inhibitor enhance the coloration of the skin.

The intersorption composition comprises the matrix components PPG 40 butyl ether and dimethyiltrimethyl polysiloxane; the active ingredients iron oxide pigments for color, titanium dioxide for UV protection, and tocopherol acetate to inhibit free radicals; pigment stabilizers to disperse the active ingredients; dispersants to further impede diffusion of the active ingredients out of the matrix; a preservative; and a volatile component.

Table 3 includes each ingredient and its amount.

TABLE 3

| Matrix | | Viscosity |
|---|---|---|
| PPG 40 Butyl Ether | 1.9% | 750 cps |
| Dimethyl/Trimethyl Polysiloxane | 12.0% | 650 cps |
|  |  | Mixture = |
|  |  | 680 cps |

| Dispersants | | HLB Value |
|---|---|---|
| PEG-40 stearate ester | 1.5% | 16.9 |
| PEG-25 lauryl ether | 1.5% | 16.9 |
| Polysorbate-20 | 4.5% | 16.7 |
| Polysorbate-40 | 1.5% | 15.6 |
| Sodium Laureth Sulfate | 1.3% | 40.0 |
|  | Total = | Average = |
|  | 10.3% | 19.5 |

| Active Ingredients | |
|---|---|
| Wackherr W9814 black iron oxide pigment | 0.5% |
| Wackherr W3801 red iron oxide pigment | 0.5% |
| Wackherr W1803 yellow iron oxide pigment | 0.5% |
| Titanium Dioxide | 1.0% |
| Tocopherol Acetate | 0.5% |
| Pigment Stabilizers | |
| Sorbitol | 2.5% |
| Glycereth-26 | 2.0% |
| Water | 10.5% |
| Preservative | |
| Methylchloroisothiazolinone | 0.05% |
| Water | 1.00% |
| Volatile Component | |
| Cyclomethicone, volatile | 56.75% |

The concentration of all components is expressed as percent by weight. The iron oxide pigments and the titanium dioxide are dispersed in the stabilizers at 40–45° C. with constant stirring. When the iron oxide pigments and the titanium dioxide are dispersed, the dispersants are added. Next, the preservative, dissolved in water, is added. The tocopherol acetate is mixed with the matrix components and added. The preparation is covered and the volatile component is added. Stirring is continued until the preparation is uniform and is cooled to room temperature. The formulation can be spread directly and easily on a substrate.

EXAMPLE 4

Example 4 illustrates the intersorption composition and method of the present invention wherein the active ingredient is the povidone iodine. Povidone iodine is an effective anti-infective agent whose use on skin has been limited because its stains the skin a yellowish brown color.

The intersorption composition comprises the matrix components PPG 40 butyl ether and dimethyl/trimethyl polysiloxane; the active ingredient povidone iodine; solubilizers to solubilize the povidone iodine; dispersants to further impede povidone iodine diffusion out of the matrix; a preservative; and a volatile component.

Table 4 includes each ingredient and its amount.

TABLE 4

| Matrix | | Viscosity |
|---|---|---|
| PPG 40 Butyl Ether | 1.9% | 750 cps |
| Dimethyl/Trimethyl Polysiloxane | 12.0% | 650 cps |
|  |  | Mixture = |
|  |  | 680 cps |

| Dispersants | | HLB Value |
|---|---|---|
| PEG-40 stearate ester | 1.5% | 16.9 |
| PEG-25 lauryl ether | 1.5% | 16.9 |
| Polysorbate-20 | 5.5% | 16.7 |
| Sodium Laureth Sulfate | 1.3% | 40.0 |
|  | Total = | Average = |
|  | 9.8% | 19.9 |

| Active Ingredient | |
|---|---|
| Povidone Iodine | 5.0% |
| Povidone Iodine Solubilizers | |
| Glycerin | 2.5% |
| Water | 12.5% |
| Volatile Components | |
| Cyclomethicone, volatile | 56.3% |

The concentration of all components is expressed as percent by weight. In a closed container, the povidone iodine is dissolved in the glycerin and water with constant stirring. The matrix components and the dispersants are added. Next, the volatile component is added. Stirring is continued until the preparation is uniform. The formulation can be spread directly and easily on a substrate such as skin.

Animal Skin Tests

Five white rabbits are used in this study. The backs of the rabbits are shaved and two squares designated A and B, four inches per side, are outlined with surgical tape on the back of each rabbit. A suspension containing $5 \times 10^6$ *Staphylococcus epidermis* is applied to each square. A solution of povidone iodine, prepared by dissolving one gram of povidone iodine in ten milliliters of water adjusted to pH 6.0 with sodium bicarbonate, is applied to square A on each subject. The intersorption composition of Example 4 is applied to square B on each subject. After eight hours, the back of each rabbit is washed with a detergent solution. Each square is wiped with a swab and the wiping is cultured for *Staphylococcus epidermis*. The A squares culture no *Staphylococcus epidermis* colonies and are colored a dark yellowish brown. The B squares culture no *Staphylococcus epidermis* colonies and are colored an almost imperceptible yellow.

EXAMPLE 5

Example 5 illustrates the intersorption composition of the present invention wherein the active ingredient is the UV protectant benzophenone-2.

The intersorption composition comprises the matrix component dimethicone (ultra high viscosity); the active ingredient benzophenone-2; solubilizers to solubilize the benzophenone-2; dispersants to further impede benzophenone-2 diffusion out of the matrix; a preservative; and a volatile component.

Table 5 includes each ingredient and its amount.

TABLE 5

| Matrix | | Viscosity |
| --- | --- | --- |
| Dimethicone, ultra high viscosity | 1.56% | 12,500 cps |
| Dispersants | | HLB Value |
| PEG-40 stearate ester | 1.5% | 16.9 |
| PEG-25 lauryl ether | 1.5% | 16.9 |
| Polysorbate-20 | 3.0% | 16.7 |
| Polysorbate-40 | 3.0% | 15.6 |
| Ceteareth-3 | 0.4% | 6.0 |
| Ceteareth-6 | 0.2% | 9.5 |
| | Total = 9.6% | Average = 15.8 |
| Active Ingredient | | |
| Benzophenone-2 | 1.0% | |
| Benzophenone-2 Solubilizers | | |
| Glycerol | 3.0% | |
| Water | 12.85% | |
| Preservative | | |
| Methylchloroisothiazolinone | 0.05% | |
| Water | 1.50% | |
| Volatile Component | | |
| Cyclomethicone, volatile D4 or D5 or mixture of D4 and D5 | 70.44% | |

The concentration of all components is expressed as percent by weight. In a closed container, the benzophenone-2 is dissolved in solubilizers at 38–42° C. with constant stirring. The dispersants are added, then the preservative is added, then the dimethicone (ultra high viscosity) is added and then the volatile component is added. The mixture is stirred until uniform and cooled to room temperature. The formulation can be spread directly and easily on a substrate such as skin.

EXAMPLE 6

Example 6 illustrates the intersorption composition of the present invention wherein the active ingredients are a fragrance, an insect repellent, metal stearates which produce luster, sheen and sparkle, and chitosan which protects against organic solvents.

The intersorption composition comprises the matrix components jojoba oil and polysiloxane polyether copolymer (Dow Corning Q2-1401); one of the active ingredients; solubilizers to solubilize the active ingredient, dispersants to further impede active ingredient diffusion out of the matrix; a preservative; and a volatile component.

Table 6 includes each ingredient and its amount.

TABLE 6

| Matrix | | Viscosity |
| --- | --- | --- |
| Jojoba Oil | 2.0% | 40 cps |
| Polysiloxane polyether copolymer (Dow Corning Q2-1401) | 2.0% | 5000 cps Mixture = 230 cps |
| Dispersants | | HLB Value |
| PEG-40 stearate ester | 1.5% | 16.9 |
| PEG-25 lauryl ether | 1.5% | 16.9 |
| Polysorbate-20 | 3.0% | 16.7 |
| Polysorbate-40 | 3.0% | 15.6 |
| | Total = 9.0% | Average = 16.3 |
| Active Ingredients | | |
| Fragrance - #8881156/Luzi A.G. or | 2.0% | |
| Insect Repellent-N,N-Diethyl-m-Toluamide or Luster Enhancer - Metallic Stearate or Protectant - Chitosan acetate | 4.0% 1.0% 0.5% | |
| Solubilizers | | |
| PEG 400 | 3.0% | |
| Glycereth-26 | 2.0% | |
| Water | 10.0% | |
| Preservative | | |
| Methylchloroisothiazolinone | 0.05% | |
| Volatile Component | | |
| Cyclomethicone 244 - add to total 100% | | |

The concentration of all components is expressed as percent by weight. Each of the active ingredients is dissolved or dispersed individually in the solubilizers at 38–42° C. with constant stirring. The dispersants and the preservative are added, then the matrix components are added. The preparations are covered and the volatile component is added. The mixtures are stirred until uniform and cooled to room temperature. The formulation can be spread directly and easily on a substrate.

EXAMPLE 7

Example 7 illustrates the intersorption composition of the present invention wherein the active ingredient is a tanning agent.

The intersorption composition comprises the matrix components jojoba oil and polysiloxane polyether copolymer (Dow Corning Q2-1401); the active ingredient dihydroxyacetone; solubilizers to solubilize the dihydroxyacetone; dispersants to further impede dihydroxyacetone diffusion out of the matrix; a preservative; and a volatile component.

Table 7 includes each ingredient and its amount.

TABLE 7

| Matrix | | Viscosity |
|---|---|---|
| Jojoba Oil | 2.0% | 40 cps |
| Polysiloxane polyether copolymer (Dow Corning Q2-1401) | 2.0% | 5000 cps Mixture = 230 cps |
| Dispersants | | HBL Value |
| PEG-40 stearate ester | 1.5% | 16.9 |
| PEG-25 lauryl ether | 1.5% | 16.9 |
| Polysorbate-20 | 3.0% | 16.7 |
| Polysorbate-40 | 3.0% | 15.6 |
| | Total = 9.0% | Average = 16.3 |
| Active Ingredient | | |
| Dihydroxyacetone | 2.5% | |
| Solubilizers | | |
| Sorbitol | 15.0% | |
| Water | 1.0% | |
| Preservative | | |
| Methylchloroisothiazolinone | 0.05% | |
| Volatile Component | | |
| Cyclomethicone 244 | 68.45% | |

The concentration of all components is expressed as percent by weight. The active ingredient is dissolved in the solubilizers at 38–42° C. with constant stirring. The dispersants and the preservative are added, then the matrix components are added. The preparations is covered and the volatile component is added. The mixture is stirred until uniform and cooled to room temperature. The formulation can be spread directly and easily on a substrate such as skin.

EXAMPLE 8

Example 8 illustrates the intersorption composition of the present invention wherein the active ingredients are a tanning agent, coloring agents and a UV dispersant.

The intersorption composition comprises: the matrix components PPG 40 butyl ether and dimethyvtrimethyl polysiloxane; the active ingredients dihydroxyacetone for tanning, iron oxide pigments for color, and titanium dioxide for UV dispersal; solubilizers to solubilize and disperse the active ingredients; dispersants to further impede active ingredient diffusion out of the matrix; a preservative; and a volatile component.

Table 8 includes each ingredient and its amount.

TABLE 8

| Matrix | | Viscosity |
|---|---|---|
| PPG 40 Butyl Ether | 1.9% | 750 cps |
| Dimethyl/Trimethyl Polysiloxane | 12.0% | 650 cps Mixture = 680 cps |
| Dispersants | | HBL Value |
| PEG-40 stearate ester | 1.5% | 16.9 |
| PEG-25 lauryl ether | 1.5% | 16.9 |
| Polysorbate-20 | 4.5% | 16.7 |

TABLE 8-continued

| Polysorbate-40 | 1.5% | 15.6 |
|---|---|---|
| Sodium Laureth Sulfate | 1.3% | 40.0 |
| | Total = 10.3% | Average = 19.5 |
| Active Ingredients | | |
| Wackherr W9814 black iron oxide pigment | 0.5% | |
| Wackherr W3801 red iron oxide pigment | 0.5% | |
| Wackherr W1803 yellow iron oxide pigment | 0.5% | |
| Titanium Dioxide | 1.0% | |
| Dihydroxyacetone | 0.5% | |
| Solubilizers | | |
| Sorbitol | 2.5% | |
| Glycereth-26 | 2.0% | |
| Alcohol | 12.5% | |
| Water | 1.0% | |
| Preservative | | |
| Methylchloroisothiazolinone | 0.05% | |
| Water | 1.00% | |
| Volatile Component | | |
| Cyclomethicone, volatile | 54.75% | |

The concentration of all components is expressed as percent by weight. Each of the active ingredients is dissolved or dispersed in the solubilizers at 40–45° C. with constant stirring. The dispersants and the preservative are added, then the matrix components are added. The preparations are covered and the volatile component is added. The mixture is stirred until uniform and cooled to room temperature. The formulation can be spread directly and easily on a substrate.

EXAMPLE 9

Example 9 illustrates the intersorption composition of the present invention wherein the active ingredients are a tanning agent and organic dye colorants.

The intersorption composition comprises the matrix components squalane and dimethicone (ultra high viscosity); the active ingredients dihydroxyacetone for tanning and organic dyes FD&C Red No. 33, Yellow No. 5 and Blue No. 1 for coloring; dispersants to further impede dihydroxyacetone and organic dye diffusion out of the matrix; a preservative; and a volatile components.

TABLE 9

| Matrix | | Viscosity |
|---|---|---|
| Squalane | 1.8% | 40 cps |
| Dimethicone, ultra high viscosity | 1.3% | 12500 cps Mixture = 150 cps |
| Dispersants | | HBL Value |
| PEG-36 Oleate ester | 1.4% | 16.9 |
| PEG-20 Cetyl ether | 1.6% | 15.7 |
| Polysorbate-20 | 6.2% | 16.7 |
| Sodium Lauryl Sulfate | 1.4% | 40.0 |
| Caprylyl Pyrroliodone | 0.8% | 6.0 |
| Lauryl Pyrroliodone | 1.0% | 3.0 |
| | Total = 12.4% | Average = 17.4 |

TABLE 9-continued

| Active Ingredients | |
| --- | --- |
| FD&C Red No. 33 | 0.033% |
| FD&C Yellow No. 5 | 0.064% |
| FD&C Blue No. 1 | 0.003% |
| Dihydroxyacetone | 1.5% |
| Solubilizers | |
| Propylene Glycol | 3.0% |
| Water | 11.8% |
| Preservative | |
| Imidazolidinyl Urea | 0.2% |
| Water | 2.0% |
| Volatile Component | |
| Cyclomethicone, volatile D4 or D5 or a mixture | 65.9% |

The concentration of all components is expressed as percent by weight. The dihydroxyacetone and the organic dyes FD&C Red No. 33, Yellow No. 5 and Blue No. 1 are dissolved in solubilizers at 38–42° C. with constant stirring. When the dihydroxyacetone and organic dyes are dissolved, the dispersants, the imidazolidinyl urea and water are added. Next the matrix components are added. The preparation is covered and the volatile component is added. Stirring is continued until the preparation is uniform and is cooled to room temperature. The formulation can be spread directly and easily on a substrate such as skin.

It should be understood, of course, that the foregoing relates only to preferred embodiments of the present invention and that numerous modifications or alterations may be made therein without departing from the spirit and the scope of the invention as set for in the appended claims.

We claim:

1. A composition comprising:
   a. a matrix having a viscosity between 100 centipoise and 20,000 centipoise, wherein the matrix comprises squalene and dimethicone;
   b. a dispersant having an average hydrophilic-lipophilic balance between 10 and 25, wherein the dispersant is selected from the group consisting of sterate esters, lauryl ethers, polysorbates, lauryl sulfates, oleate esters, cetyl ethers, ceteareths, pyrrolidones and combinations thereof; and,
   c. a coloring active ingredient, wherein the coloring active ingredient is selected from the group consisting of FD&C Red No. 33, FD&C Yellow No. 5 and FD&C Blue No. 1 and combinations thereof, wherein the matrix and the dispersant substantially prevent penetration of the coloring active ingredient into skin.

2. The composition of claim 1, wherein the matrix has a viscosity between 100 centipoise and 12500 centipoise.

3. The composition of claim 1, wherein the dispersant has an average hydrophilic-lipophilic balance between 15 and 20.

4. A method for delivering an active ingredient onto a permeable surface, comprising the step of applying to the permeable surface a composition comprising:
   a. a matrix having a viscosity between 100 centipoise and 20,000 centipoise, wherein the matrix comprises squalene and dimethicone;
   b. a dispersant having an average hydrophllic-lipophilic balance between 10 and 25, wherein the dispersant is selected from the group consisting of sterate esters, lauryl ethers, polysorbates, lauryl sulfates, oleate esters, cetyl ethers, ceteareths, pyrrolidones and combinations thereof; and,
   c. a coloring active ingredient, wherein the coloring active ingredient is selected from the group consisting of FD&C Red No. 33, FD&C Yellow No. 5 and FD&C Blue No. 1 and combinations thereof, wherein the matrix and the dispersant substantially prevent penetration of the coloring active ingredient into skin.

5. The method of claim 4, wherein the matrix has a viscosity between 100 centipoise and 12,500 centipoise.

6. The method of claim 4, wherein the dispersant has an average hydrophilic-lipophilic balance between 15 and 20.

7. A composition comprising:
   a. a matrix comprising squalene and dimethicone;
   b. a dispersant selected from the group consisting of stearate esters, lauryl ethers, polysorbates, lauryl sulfates, oleate esters, cetyl ethers, ceteareths and pyrrolidones; and
   c. a coloring active ingredient selected from the group consisting of FD&C Red No. 33, FD&C Yellow No. 5 and FD&C Blue No. 1,
   wherein the matrix and dispersant substantially prevent penetration of the coloring active ingredient into skin.

8. The composition of claim 7, wherein the matrix has a viscosity between 100 centipoise and 20,000 centipoise.

9. A composition comprising:
   a. a matrix comprising squalene and dimethicone;
   b. a dispersant selected from the group consisting of stearate esters, lauryl ethers, polysorbates, lauryl sulfates, oleate esters, cetyl ethers, ceteareths, pyrrolidones and combinations thereof, and
   c. a coloring active ingredient, wherein the coloring active ingredient is selected from the group consisting of FD&C Red No. 33, FD&C Yellow No. 5, FD&C Blue No. 1, and combinations thereof,
   wherein the matrix and dispersant substantially prevent penetration of the coloring active ingredient into skin.

10. The composition of claim 9, wherein the matrix has a viscosity between 100 centipoise and 20,000 centipoise.

11. A composition consisting essentially of:
    a. a matrix comprising squalene and dimethicone;
    b. a dispersant selected from the group consisting of sterate esters, lauryl ethers, polysorbates, lauryl sulfates, oleate esters, cetyl ethers, ceteareths, pyrrolidones and combinations thereof; and
    c. a coloring active ingredient selected from the group consisting of FD&C Red No. 33, FD&C Yellow No. 5 and FD&C Blue No. 1 and combinations thereof,
    wherein the matrix and the dispersant substantially prevent penetration of the coloring active ingredient into skin.

12. The composition of claim 11, wherein the matrix has a viscosity between 100 centripoise and 20,000 centipoise.

13. A composition comprising:
    a. a matrix comprising squalene and dimethicone;
    b. a dispersant selected from the group consisting of stearate esters, lauryl ethers, polysorbates, lauryl sulfates, oleate esters, cetyl ethers, ceteareths, pyrrolidones and combinations thereof; and
    c. a medicinally active ingredient selected from the group consisting of gentian violet and povidone iodine,
    wherein the matrix and dispersant substantially prevent penetration of the medicinally active ingredient into skin but maintain the medicinally active ingredient in contact with the surface of the skin.

14. The composition of claim 13, wherein the matrix has a viscosity between 100 centipoise and 20,000 centipoise.

15. The composition of claim 13, wherein the matrix has a viscosity between 100 centipoise and 12,500 centipoise.

16. The composition of claim 13, wherein the dispersant has an average hydrophilic-lipophilic balance between 10 and 25.

17. The composition of claim 13, wherein the dispersant has an average hydrophilic-lipophilic balance between 15 and 20.

18. A method for delivering an active ingredient to the surface of skin while substantially preventing the penetration of the active ingredient into the skin, comprising the step of applying to the skin a composition comprising:
  a. a matrix comprising squalene and dimethicone;
  b. a dispersant selected from the group consisting of stearate esters, lauryl ethers, polysorbates, lauryl sulfates, oleate esters, cetyl ethers, cetearehts, pyrrolidones and combinations thereof; and
  c. a medicinally active ingredient selected from the group consisting of gentian violet and povidone iodine,
  wherein the matrix and dispersant substantially prevent penetration of the medicinally active ingredient into skin but maintain the medicinally active ingredient in contact with the surface of the skin.

19. The composition of claim 18, wherein the matrix has a viscosity between 100 centipoise and 20,000 centipoise.

20. The composition of claim 18, wherein the matrix has a viscosity between 100 centipoise and 12,500 centipoise.

21. The composition of claim 18, wherein the dispersant has an average hydrophilic-lipophilic balance between 10 and 25.

22. The composition of claim 18, wherein the dispersant has an average hydrophilic-lipophilic balance between 15 and 20.

23. A composition comprising:
  a. a matrix comprising squalene and dimethicone;
  b. a dispersant selected from the group consisting of stearate esters, lauryl ethers, polysorbates, lauryl sulfates, oleate esters, cetyl ethers, cetearehts, pyrrolidones and combinations thereof, wherein the dispersant is present in an average amount of 5 to 20 percent by weight; and
  c. an coloring active ingredient selected from the group consisting of black iron oxide pigment, red iron oxide pigment, yellow iron oxide pigment, titanium dioxide, tocopherol acetate, dihydroxyacetone and combinations thereof, wherein the matrix and dispersant substantially prevent penetration of the coloring active ingredient into skin but maintain the active ingredient in contact with the surface of the skin.

24. The composition of claim 23, the matrix has a viscosity between 100 centipoise and 20,000 centipoise.

25. The composition of claim 23, wherein the matrix has a viscosity between 100 centipoise and 12,500 centipoise.

26. The composition of claims 23, wherein the dispersant has an average hydrophilic-lipophilic balance between 10 and 25.

27. The composition of claim 23, wherein the dispersant has an average hydrophilic-lipophilic balance between 15 and 20.

28. A composition comprising:
  a. a matrix comprising squalene and dimethicone;
  b. a dispersant selected from the group consisting of stearate esters, lauryl ethers, polysorbates, lauryl sulfates, oleate esters, cetyl ethers, cetearehts, pyrrolidones and combinations thereof; and
  c. an active ingredient selected from the group consisting of benzophenone-2, dihydroxyacetone and N,N-diethyl-m-toluamide,
  wherein the matrix and dispersant substantially prevent penetration of the active ingredient into skin but maintain the active ingredient in contact with the surface of the skin.

29. The composition of claim 28, wherein the matrix has a viscosity between 100 centipoise and 20,000 centipoise.

30. The composition of claim 28, wherein the matrix has a viscosity between 100 centipoise and 12,500 centipoise.

31. The composition of claim 28, wherein the dispersant has an average hydrophilic-lipophilic balance between 10 and 25.

32. The composition of claim 28, wherein the dispersant has an average hydrophilic-lipophilic balance between 15 and 20.

33. A composition for preventing the absorption of one or more active ingredients into the skin comprising:
  a. a matrix comprising squalene and dimethicone and having a viscosity between 100 centipoise and 20,000 centipoise;
  b. a dispersant selected from the group consisting of stearate esters, lauryl ethers, polysorbates, lauryl sulfates, oleate esters, cetyl ethers, cetearehts, pyrrolidones and combinations thereof, wherein the dispersant has an average hydrophilic-lipophilic balance between 10 and 25 and is present in an average amount of 5 to 20 percent by weight; and
  c. an active ingredient selected from the group consisting of insoluble colorants, soluble colorants antifungal agents, antimicrobial agents antibiotics, fragrances, sunscreens, insect repellents and surface tanning agents.
  wherein the matrix and dispersant form a protective layer on the skin's surface which substantially prevents the penetration of the active ingredients present in the composition into the skin.

34. The composition of claim 33, wherein the matrix has a viscosity between 100 centipoise and 12,500 centipoise.

35. The composition of claim 33, wherein the dispersant has an average hydrophilic-lipophilic balance between 15 and 20.

36. A method for preventing the absorption of one or more active ingredients into the skin comprising the step of applying to the skin a composition comprising:
  a. a matrix comprising squalene and dimethicone and having a viscosity between 100 centipoise and 20,000 centipoise;
  b. a dispersant selected from the group consisting of stearate esters, lauryl ethers, polysorbates, lauryl sulfates, oleate esters, cetyl ethers, cetearehts, pyrrolidones and combinations thereof, wherein the dispersant has an average hydrophilic-lipophilic balance between 10 and 25; and
  c. an active ingredient selected from the group consisting of insoluble colorants, soluble colorants, antifungal agents, antimicrobial agents, antibiotics, fragrances, sunscreens, insect repellents and surface tanning agents.
  wherein the matrix and dispersant form a protective layer on the skin's surface which substantially prevents the penetration of the active ingredients present in the composition into the skin.

37. The method of claim 36, wherein the matrix has a viscosity between 100 centipoise and 12,500 centipoise.

38. The method of claim 36, wherein the dispersant has an average hydrophilic-lipophilic balance between 15 and 20.

39. A method for preventing the absorption of one or more active ingredients into the skin comprising the step of applying to the skin a composition comprising:

a. a matrix comprising squalene and dimethicone;

b. a dispersant selected from the group consisting of stearate esters, lauryl ethers, polysorbates, lauryl sulfates, oleate esters, cetyl ethers, cetearaths, pyrrolidones and combinations thereof, and c. an active ingredient selected from the group consisting of insoluble colorants, soluble colorants, dirt, soot, antifungal agents, antimicrobial agents, antibiotics, fragrances, sunscreens, insect repellents and surface tanning agents, wherein the matrix and dispersant form a protective layer on the skin's surface which substantially prevents the penetration of the active ingredients present in the composition into the skin.

40. The composition of claim 39, wherein the matrix has a viscosity between 100 centipoise and 20,000 centipoise.

41. The composition of claim 39, wherein the matrix has a viscosity between 100 centipoise and 12,500 centipoise.

42. The composition of claim 39, wherein the dispersant has an average hydrophilic-lipophilic balance between 10 and 25.

43. The composition of claim 39, wherein the dispersant has an average hydrophilic-lipophilic balance between 15 and 20.

44. A method for preventing the absorption of one or more active ingredients into the skin comprising the step of applying to the skin a composition comprising:

a. a matrix comprising squalene and dimethicone;

b. a dispersant selected from the group consisting of stearate esters, lauryl ethers, polysorbates, lauryl sulfates, oleate esters, cetyl ethers, cetearaths, pyrrolidones and combinations thereof; and c. an active ingredient selected from the group consisting of insoluble colorants, soluble colorants, antifungal agents, antimicrobial agents, antibiotics, fragrances, sunscreens, insect repellents and surface tanning agents, wherein the matrix and dispersant form a protective layer on the skin's surface which substantially prevents the penetration of the active ingredients present in the composition into the skin.

45. The composition of claim 44, wherein the matrix has a viscosity between 100 centipoise and 20,000 centipoise.

46. The composition of claim 44, wherein the matrix has a viscosity between 100 centipoise and 12,500 centipoise.

47. The composition of claim 44, wherein the dispersant has an average hydrophilic-lipophilic balance between 10 and 25.

48. The composition of claim 44, wherein the dispersant has an average hydrophilic-lipophilic balance between 15 and 20.

49. The composition of claim 23, wherein the dispersant is present in an average amount of 8 to 14 percent by weight.

50. The composition of claim 33, wherein the dispersant is present in an average amount of 8 to 14 percent by weight.

51. A composition comprising:

a. a matrix comprising squalene and dimethicone;

b. a dispersant selected from the group consisting of stearate esters, lauryl ethers, polysorbates, lauryl sulfates, oleate esters, cetyl ethers, cetearaths, pyrrolidones and combinations thereof 25, wherein the dispersant is present in an average amount of 5 to 20 percent by weight; and c. an coloring active ingredient selected from the group consisting of soluble anionic dyes, soluble cationic dyes, insoluble pigments and combinations thereof, wherein the matrix and dispersant substantially prevent penetration of the active ingredient into skin but maintain the active ingredient in contact with the surface of the skin.

* * * * *

UNITED STATES PATENT AND TRADEMARK OFFICE
CERTIFICATE OF CORRECTION

PATENT NO. : 6,024,968
DATED : February 15, 2000
INVENTOR(S) : H.R. Süess et al.

Page 1 of 2

It is certified that error appears in the above-identified patent and that said Letters Patent is hereby corrected as shown below:

| COLUMN | LINE | |
|---|---|---|
| 1 (Claim 1, | 50 line 14) | "wherein the matrix..." should begin a new paragraph |
| 1 (Claim 2, | 54 line 2) | "12500" should read --12,500-- |
| 18 (Claim 4, | 7 line 16) | "wherein the matrix..." should begin a new paragraph |
| 18 (Claim 9, | 33 line 6) | "thereof," should read --thereof;-- |
| 18 (Claim 12, | 56 line 2) | "centripoise" should read --centipoise-- |
| 19 (Claim 23, | 46 line 9) | "an coloring" should read --a coloring-- |
| 18 (Claim 23, | 50 line 13) | "wherein the matrix..." should begin a new paragraph |
| 19 (Claim 24, | 54 line 1) | after "claim 23," insert --wherein-- |
| 19 (Claim 26, | 58 line 1) | "claims 23" should read --claim 23-- |
| 20 (Claim 33, | 33 line 14) | after "colorants" insert --,-- |

UNITED STATES PATENT AND TRADEMARK OFFICE
CERTIFICATE OF CORRECTION

PATENT NO. : 6,024,968
DATED : February 15, 2000
INVENTOR(S) : H.R. Süess et al.

Page 2 of 2

It is certified that error appears in the above-identified patent and that said Letters Patent is hereby corrected as shown below:

| COLUMN | LINE | |
|---|---|---|
| 20 (Claim 33, | 33 line 14) | after "agents" insert --,-- |
| 20 (Claim 33, | 33 line 14) | "agents." should read --agents,-- |
| 20 (Claim 36, | 63 line 17) | "agents." should read --agents,-- |
| 21 (Claim 39, | 12 line 8) | "thereof," should read --thereof;-- |
| 22 (Claim 51, | 29 line 6) | delete "25" |
| 22 (Claim 51, | 32 line 9) | "an coloring" should read --a coloring-- |

Signed and Sealed this

Third Day of April, 2001

*Attest:*

NICHOLAS P. GODICI

*Attesting Officer*  Acting Director of the United States Patent and Trademark Office